United States Patent [19]

Rice et al.

[11] Patent Number: 5,401,755
[45] Date of Patent: Mar. 28, 1995

[54] N-(1-THIENYLCYCLOALKYL)ALKENYLAMINES FOR TREATMENT OF NEUROTOXIC INJURY

[75] Inventors: Kenner C. Rice, Rockville; Arthur E. Jacobson, Potomac; Andrew Thurkauf, Laurel; Mariena V. Mattson, Rockville, all of Md.; Thomas L. O'Donohue, Chesterfield, Mo.; Patricia C. Contreras, Ballwin, Mo.; Nancy M. Gray, Ellisville, Mo.

[73] Assignees: G. D. Searle & Co., Skokie, Ill.; National Institutes of Health, Rockville, Md.

[21] Appl. No.: 774,003

[22] Filed: Oct. 8, 1991

Related U.S. Application Data

[63] Continuation of Ser. No. 125,025, Nov. 24, 1987, abandoned.

[51] Int. Cl.⁶ .................... C07D 409/08; A61K 31/44
[52] U.S. Cl. ...................................... 514/336; 546/284
[58] Field of Search ...................... 546/284; 514/336

[56] References Cited

U.S. PATENT DOCUMENTS

4,598,153  7/1986  Rice et al. ............................ 546/229

OTHER PUBLICATIONS

Chem. Abstracts, vol. 107 (23) abst. No. 211, 790-y Dec. 7, 1987.
Chem Abstracts, vol. 107, Chemical Substance Index (Ph-Pz) p. 7975 CS Dec. 31, 1987.
Chem. Abstracts, vol. 107, Formula-*Index* C₁₃-C₂₁, p. 1663-F Dec. 31, 1987.
S. M. Rothman and J. W. Olney, *Annals of Neurology*, vol. 19, No. 2, 105-111 (1986).

N. A. Anis et al., *Br. J. Pharmacol.*, 79, 565-575 (1983).
J. W. Olney et al., *Neuroscience Letters*, 68, 29-34 (1986).
S. C. Berry et al., *Eur. J. Pharm.*, 96, 261-267 (1983).
M. E. Goldman et al., *FEBS Lett.*, 190, 333-336 (1985).
R. Quirion, *Proc. Nat'l. Acad. Sci. USA*, 78, 5881-5885 (1981).
L. D. Snell et al., *J. Pharmacol. Exp. Ther.*, 235, No. 1, 50-57 (1985).

*Primary Examiner*—Alan L. Rotman
*Attorney, Agent, or Firm*—J. Timothy Keane; Frank S. Ungemach

[57] ABSTRACT

Compounds, compositions and methods of treatment are described to control brain damage associated with anoxia or ischemia which typically follows stroke, cardiac arrest or perinatal asphyxia. The treatment includes administration of an N-(1-thienylcycloalkyl)alkenylamine compound as an antagonist to inhibit excitotoxic actions at major neuronal excitatory amino acid receptor sites. Compounds of most interest are those of the formula

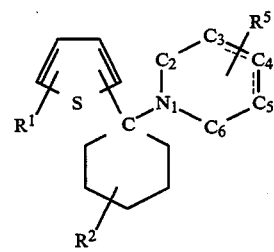

wherein $R^1$, $R^2$, and $R^5$ are defined in specification.

13 Claims, No Drawings

N-(1-THIENYLCYCLOALKYL)ALKENYLAMINES FOR TREATMENT OF NEUROTOXIC INJURY

This is a continuation of application Ser. No. 07/125,025, filed Nov. 24, 1987, now abandoned.

FIELD OF THE INVENTION

This invention is in the field of clinical neurology and relates specifically to compounds, compositions and methods for neuroprotective purposes such as controlling brain damage which occurs during periods of anoxia or ischemia associated with stroke, cardiac arrest or perinatal asphyxia.

BACKGROUND OF THE INVENTION

Unlike other tissue which can survive extended periods of hypoxia, brain tissue is particularly sensitive to deprivation of oxygen or energy. Permanent damage to neurons can occur during brief periods of hypoxia, anoxia or ischemia. Neurotoxic injury is known to be caused or accelerated by certain excitatory amino acids (EAA) found naturally in the central nervous system (CNS). Glutamate (Glu) is an endogenous amino acid which was early characterized as a fast excitatory transmitter in the mammalian brain. Glutamate is also known as a powerful neurotoxin capable of killing CNS neurons under certain pathological conditions which accompany stroke and cardiac arrest. Normal glutamate concentrations are maintained within brain tissue by energy-consuming transport systems. Under low energy conditions which occur during periods of hypoglycemia, hypoxia or ischemia, cells can release glutamate. Under such low energy conditions the cell is not able to take glutamate back into the cell. Initial glutamate release stimulates further release of glutamate which results in an extracellular glutamate accumulation and a cascade of neurotoxic injury.

It has been shown that the sensitivity of central neurons to hypoxia and ischemia can be reduced by either interfering with synaptic transmission through blockade of the sodium or calcium ion channel or by the specific antagonism of postsynaptic glutamate receptors [see S. M. Rothman and J. W. Olney, "Glutamate and the Pathophysiology of Hypoxia - Ischemic Brain Damage," *Annals of Neurology*, Vol. 19, No. 2 (1986)]. Glutamate is characterized as a broad spectrum agonist having activity at three neuronal excitatory amino acid receptor sites. These receptor sites are named after the amino acids which selectively excite them, namely: Kainate (KA), N-methyl-D-aspartate (NMDA or NMA) and quisqualate (QUIS). Glutamate is believed to be a mixed agonist capable of binding to and exciting all three receptor types.

Neurons which have EAA receptors on their dendritic or somal surfaces undergo acute excitotoxic degeneration when these receptors are excessively activated by glutamate. Thus, agents which selectively block or antagonize the action of glutamate at the EAA synaptic receptors of central neurons can prevent neurotoxic injury associated with anoxia, hypoxia or ischemia caused by stroke, cardiac arrest or perinatal asphyxia.

Phencyclidine (PCP) and the PCP-like compound ketamine have been found to reduce selectively the excitatory effects of NMDA as compared to KA and QUIS [Anis, N. A. et al, "The Dissociative Anaesthetics, Ketamine and Phencyclidine, Selectively Reduce Excitation of Central Mammalian Neurones by N-Methyl-Aspartate", *Br. J. Pharmacol.*, 79, 565 (1983)]. Other compounds having PCP-like properties such as cyclazocine, kynurenate and various barbiturates such as secobarbital, amobarbital and pentobarbital, have been tested as antagonists in blocking NMDA- or KA-induced neurotoxicity [J. W. Olney et al., "The Anti-Excitotoxic Effects of Certain Anesthetics, Analgesics and Sedative-Hypnotics," *Neuroscience Letters*, 68, 29-34 (1986)].

A correlation has been found between the PCP binding effects of some PCP-derivative stereoisomers and NMDA antagonism. For example, the stereoselective effects of cis-N-(1-phenyl-4-methylcyclohexyl)piperidine and (+)-1-(1-phenylcyclohexyl)-3-methylpiperidine [(+)-PCMP] over each of their corresponding isomer counterparts in reducing the excitatory action of NMDA have been confirmed in binding and behavioral data [S. D. Berry et al, "Stereoselective Effects of Two Phencyclidine Derivatives on N-Methylaspartate Excitation of Spinal Neurones in the Cat and Rat", *Eur. J. Pharm.*, 96, 261-267 (1983)]. Also, the compound (+)-PCMP has been found to be a potent inhibitor of the specific binding of [$^3$H]PCP to rat cerebral cortical membranes [M. E. Goldman et al, "Differentiation of [$^3$H]Phencyclidine and (+)-[$^3$H]SKF-10,047 Binding Sites in Rat Cerebral Cortex", *FEBS Lett.*, 170, 333-336 (1985)].

Other neurochemical mechanisms by which PCP alters behavior are known. For example, binding assays of the PCP/sigma site have been used to evaluate arylcycloalkylamines [R. Quirion, "Phencyclidine (Angel Dust)/Sigma 'Opiate' Receptor: Visualization by Tritium-Sensitive Film", *Proc. Natl. Acad. Sci. U.S.A.*, 78, 5881 (1981)]. PCP-like drugs may induce ipsilateral turning in rats by action on the PCP/sigma receptor as indicated by studies with arylcycloalkylamines, sigma-agonist benzomorphans and 1,3-dioxolanes.

These PCP-like classes of compounds have been found to inhibit NMDA-induced acetylcholine (ACh) release and such ACh release has been correlated with their affinity for the PCP receptor and with behavioral activity [L. D. Snell et al, "Antagonism of N-Methyl-D-Aspartate-Induced Transmitter Release in the Rat Striatum by Phencyclidine-Like Drugs and its Relationship to Turning Behavior", *J. Pharmacol.Exp. Ther.*, 235, No. 1, 50-56 (1985)].

U.S. Pat. No. 4,598,153 to Rice et al. describes a class of compounds, characterized as the "metaphit" family of compounds, which are useful to block receptors of phencyclidine and PCP-like compounds such as ketamine, thereby antagonizing the in vitro effects of PCP and PCP-like compounds. These "metaphit" compounds are shown in particular as acylating agents of the [$^3$H]-phencyclidine binding site. Included in the "metaphit" family of compounds are the following:

1-[1-(3-isothiocyanatophenyl)cyclohexyl]piperidine;
1-[1-(2-(4-isothiocyanato)thienyl)cyclohexyl]piperidine;
N-[1-(m-isothiocyanatophenyl)cyclohexyl]ethylamine;
N-[1-(m-(α-bromoacetylamino)phenyl)cyclohexyl]ethylamine; and
N-[1-(m-isothiocyanatophenyl)cyclohexyl]isopropylamine.

DESCRIPTION OF THE INVENTION

Control of neuropathological processes and the neurodegenerative consequences thereof in mammals is provided by treating a mammal susceptible to neurotoxic injury with an anti-excitotoxic effective amount of a compound of a class of N-(1-thienylcycloalkyl)alkenylamines represented by Formula I:

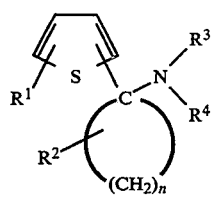

(I)

wherein $R^1$ is one or more groups selected from hydrido, alkyl, cycloalkyl, haloalkyl, alkenyl, alkynyl, hydroxyl, hydroxyalkyl, alkoxy, alkoxyalkyl, amino, halo, cyano, nitro and mercapto; wherein $R^2$ is one or more groups selected from hydrido, alkyl, cycloalkyl, haloalkyl, alkenyl, alkynyl, oxo, thio, hydroxyl, hydroxyalkyl, alkoxy, alkoxyalkyl, amino, halo, nitro, cyano and mercapto, wherein n is an integer selected from three through eight; wherein each of $R^3$ and $R^4$ is a group independently selected from hydrido, alkyl, alkenyl, alkynyl, cycloalkyl, cycloalkenyl and cycloalkynyl, and wherein $R^3$ and $R^4$ may be taken together to form a partially unsaturated N-containing cyclic group having three to eight ring carbon atoms, any one of said groups being optionally substituted with one or more substituents selected from alkyl, cycloalkyl, haloalkyl, hydroxyalkyl, alkenyl, alkynyl, oxo, hydroxyl, alkoxy, thio, alkoxyalkyl, amino, halo, cyano and mercapto; or a pharmaceutically-acceptable salt thereof.

The compounds of Formula I are further characterized by the requirement or proviso that at least one of $R^3$ and $R^4$ is a group, or $R^3$ and $R^4$ taken together form a group, which contains at least one carbon-carbon unsaturated bond.

A preferred class of compounds within Formula I consists of those compounds wherein $R^1$ is one or more groups selected from hydrido, alkyl, cycloalkyl alkenyl, hydroxyl, alkoxy, and halo; wherein $R^2$ is one or more groups selected from hydrido, alkyl, cycloalkyl, alkenyl, oxo, hydroxyl, alkoxy and halo; wherein n is an integer selected from four through seven; and wherein at least one of $R^3$ and $R^4$ is an alkenyl group of two to about twenty carbon atoms. Within this preferred class are those compounds wherein $R^3$ and $R^4$ taken together form an N-containing cyclic ring having four to eight ring carbon atoms, at least two of which ring carbon atoms are connected by a double bond.

A more preferred class of compounds within Formula I consists of those compounds of Formula II:

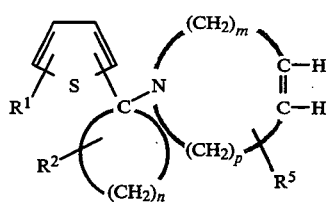

(II)

wherein $R^1$ is one or more groups selected from hydrido, alkyl of one to about ten carbon atoms, cycloalkyl of three to about ten carbon atoms, alkenyl of two to about ten carbon atoms, hydroxyl, alkoxy and halo; wherein $R^2$ is one or more groups selected from hydrido, alkyl of one to about ten carbon atoms, cycloalkyl of three to about ten carbon atoms, alkenyl of two to about ten carbon atoms, hydroxyl, oxo, alkoxy and halo; wherein $R^5$ is one or more groups selected from hydrido, alkyl of one to about ten carbon atoms, cycloalkyl of three to about ten carbon atoms, alkenyl of two to about ten carbon atoms, hydroxyl, oxo, alkoxy and halo; wherein n is an integer selected from five, six and seven, and each of m and p is an integer independently selected from one, two and three.

A more particularly preferred class of compounds within Formula I consists of those compounds

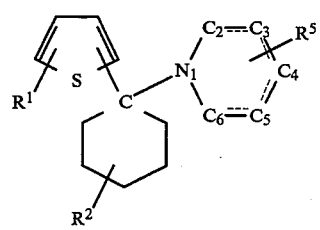

(III)

wherein $R^1$ is one or more groups selected from hydrido, alkyl of one to about ten carbon atoms, cycloalkyl of three to about ten carbon atoms, alkenyl of two to about ten carbon atoms, hydroxyl, alkoxy and halo; wherein each of $R^2$ is one or more groups selected from hydrido, alkyl of one to about ten carbon atoms, cycloalkyl of three to about ten carbon atoms, alkenyl of two to about ten carbon atoms, hydroxyl, oxo, alkoxy and halo; wherein $R^5$ is one or more groups selected from hydrido, alkyl of one to about ten carbon atoms, cycloalkyl of three to about ten carbon atoms, alkenyl of two to about ten carbon atoms, hydroxyl and alkoxy; and wherein the broken line within the N-containing ring represents a double bond between any two adjacent carbon atoms involving the 2-, 3-, 4-, 5- and 6-positions of the N-containing ring.

A more highly preferred class of compounds of Formula I consists of those compounds wherein at least one of $R^3$ and $R^4$ is a group, or $R^3$ and $R^4$ taken together form a group, which contains at least one carbon-carbon unsaturated bond other than with a carbon which is adjacent to, or in alpha-position with, the nitrogen atom of Formula I, with the proviso that such compounds are devoid of carbon-carbon unsaturation involving a carbon in alpha-position with the nitrogen atom of Formula I.

A most preferred class of compounds within Formula I consists of those compounds of Formula IV:

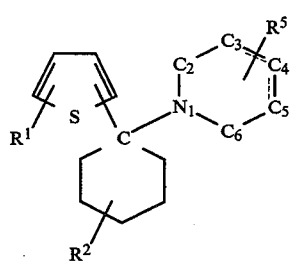

(IV)

wherein $R^1$ is one or more groups selected from hydrido, alkyl of one to about five carbon atoms, cycloalkyl of three to about five carbon atoms, alkenyl of two to about five carbon atoms, hydroxyl and alkoxy; wherein each of $R^2$ is one or more groups selected from hydrido, alkyl of one to about five carbon atoms, cycloalkyl of three to about five carbon atoms, alkenyl of two to about five carbon atoms, hydroxyl, oxo and alkoxy; wherein $R^5$ is one or more groups selected from hydrido, alkyl of one to about five carbon atoms, cycloalkyl of three to about five carbon atoms, alkenyl of two to about five carbon atoms, hydroxyl and alkoxy; and wherein the broken line within the N-containing ring represents a double bond between any two adjacent carbon atoms involving the 3-, 4- and 5-positions of the N-containing ring.

The term "hydrido" denotes a single hydrogen atom (H) which may be attached, for example, to a carbon atom or attached to an oxygen atom to form an hydroxyl group. Where the term "alkyl" is used, either alone or within other terms such as "haloalkyl" and "hydroxyalkyl", the term "alkyl" embraces linear or branched radicals having one to about twenty carbon atoms or, preferably, one to about ten carbon atoms. More preferred alkyl radicals are "lower alkyl" radicals having one to about five carbon atoms. The term "cycloalkyl" embraces cyclic radicals having three to about ten ring carbon atoms, preferably three to about five carbon atoms, such as cyclopropyl and cyclobutyl. The term "haloalkyl" embraces radicals wherein any one or more of the alkyl carbon atoms is substituted with one or more halo groups, preferably selected from bromo, chloro and fluoro. Specifically embraced by the term "haloalkyl" are monohaloalkyl, dihaloalkyl and polyhaloalkyl groups. A monohaloalkyl group, for example, may have either a bromo, a chloro, or a fluoro atom within the group. Dihaloalkyl and polyhaloalkyl groups may be substituted with two or more of the same halo groups, or may have a combination of different halo groups. A dihaloalkyl group, for example, may have two bromo atoms, such as a dibromomethyl group, or two chloro atoms, such as a dichloromethyl group, or one bromo atom and one chloro atom, such as a bromochloromethyl group. Examples of a polyhaloalkyl are trifluoromethyl, 2,2,2-trifluoroethyl, perfluoroethyl and 2,2,3,3-tetrafluoropropyl groups. The terms "alkylol" and "hydroxyalkyl" embrace linear or branched alkyl groups having one to about ten carbon atoms any one of which may be substituted with one or more hydroxyl groups. The term "alkenyl" embraces linear or branched radicals having two to about twenty carbon atoms, preferably three to about ten carbon atoms, and containing at least one carbon-carbon double bond. The term "alkynyl" embraces linear or branched radicals having two to about twenty carbon atoms, preferably two to about ten carbon atoms, and containing at least one carbon-carbon triple bond. The terms "cycloalkenyl" and "cycloalkynyl" embrace cyclic radicals having three to about ten ring carbon atoms including, respectively, one or more double or triple bonds involving adjacent ring carbons. The terms "alkoxy" and "alkoxyalkyl" embrace linear or branched oxy-containing radicals having alkyl portions of one to about ten carbon atoms, such as methoxy group. The "alkoxy" or "alkoxyalkyl" radicals may be further substituted with one or more halo atoms, such as fluoro, chloro or bromo, to provide haloalkoxy or haloalkoxyalkyl groups.

Specific examples of alkyl groups are methyl, ethyl, n-propyl, isopropyl, n-butyl, sec-butyl, iso-butyl, tert-butyl, n-pentyl, iso-pentyl, methylbutyl, dimethylbutyl and neopentyl. Typical alkenyl and alkynyl groups may have one unsaturated bond, such as an allyl group, or may have a plurality or unsaturated bonds, with such plurality of bonds either adjacent, such as allene-type structures, or in conjugation, or separated by several saturated carbons.

Included within the family of compounds of Formulas I-IV are the tautomeric forms of the described compounds, isomeric forms including diastereoisomers, and the pharmaceutically-acceptable salts thereof. The term "pharmaceutically-acceptable salts" embraces salts commonly used to form alkali metal salts and to form addition salts of free acids or free bases. Since the compounds of Formulas I-IV contain basic nitrogen atoms, such salts are typically acid addition salts or quaternary salts. The nature of the salt is not critical, provided that it is pharmaceutically acceptable, and acids which may be employed to form such salts are, of course, well known to those skilled in this art. Examples of acids which may be employed to form pharmaceutically acceptable acid addition salts include such inorganic acids as hydrochloric acid, sulphuric acid and phosphoric acid, and such organic acids as maleic acid, succinic acid and citric acid. Other pharmaceutically acceptable salts include salts with alkali metals or alkaline earth metals, such as sodium, potassium, calcium and magnesium, or with organic bases, such as dicyclohexylamine. All of these salts may be prepared by conventional means by reacting, for example, the appropriate acid or base with the corresponding compound of Formulas I-IV.

Compounds of Formulas I-IV may be prepared in accordance with the following general procedures:

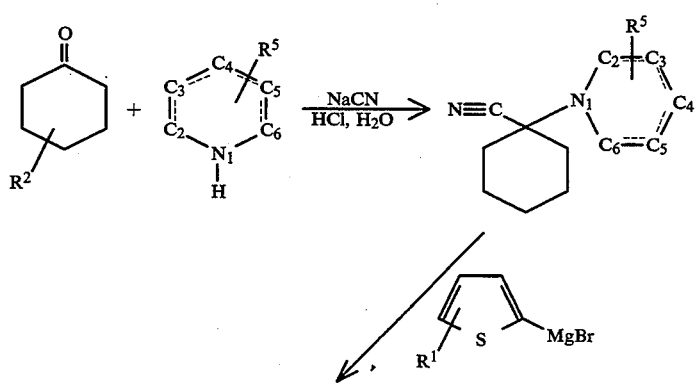

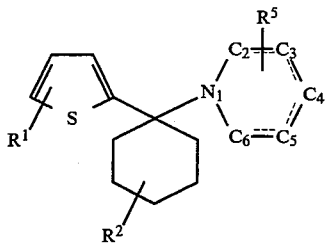

With reference to the foregoing scheme, a solution of one equivalent of the amine in water is adjusted to pH 3–4 with conc. HCl and treated with one equivalent of KCN followed by one equivalent of the ketone. The resulting mixture is stirred for one to four days, followed by the filtration of the desired white solid aminonitrile. After drying, the aminonitrile is dissolved in ether and added to a solution of 2 to 4 equivalents of the Grignard reagent generated from the arylhalide in ether. The solution is stirred 3 to 4 days, followed by extractive workup. The desired product is generally isolated as the hydrochloride salt from isopropanol/ether. For the compounds containing hydroxyl groups, the group is protected at the ketone stage with an appropriate blocking group, e.g., 2-methoxyethoxymethyl. The stereoisomeric products for some of the derivatives may be separated using classical chromatographic techniques. All ketone, amine and arylhalide starting materials and reactants are commercially available or accessible using literature procedures.

EXAMPLE I—PROCEDURE A

A reaction vessel was charged with 19.62 g (200 mmol) cyclohexanone, 20.2 g (200 mmol) 4-hydroxypiperidine and 100 ml water. To this mixture was added 16.7 ml 37% HCl to adjust the mixture to about pH 2. Then there was added sufficient 1N NaOH to adjust the mixture to about pH 4.5. The mixture was cooled and 50 ml ethanol was added followed by 10.00 g (204 mmol) NaCN. Crystalline material separated from the mixture overnight. The mixture was diluted with 400 ml water and then filtered. The filtered-out material was washed with water and then dried under reduced pressure for 3 hours at about 50° C. and then dried overnight at about 25° C. There was recovered 31.7 g of crystalline material having a m.p. of 111°–114° C. which was identified as 1-(1-cyanocyclohexyl)-4-hydroxypiperdine. A reaction vessel was charged with 200 ml ethyl ether and 0.35 mole 2-thienylmagnesium bromide. Then 36.33 g (175 mmol) of 1-(1-cyanocyclohexyl)-4-hydroxypiperidine in 200 ml tetrahydrofuran was added to the reaction vessel. An exothermic reaction was observed. After 2 hours under reflux conditions, TLC analysis showed unreacted nitrile present in the reaction mixture and the batch gave a negative result on the Gilman test. The reaction mixture stood overnight and 0.35 mole 2-thienylmagnesium bromide was added. An exothermic reaction was observed. The mixture refluxed for 2 hours. The mixture was allowed to stand overnight. A crude base product was recovered and then heated to solution in 200 ml of isopropanol. This solution was treated with 20 ml of 48% HBr to yield a crystalline material. This mixture was cooled to about 25° C. and filtered. The precipated material was washed with isopropanol to give 53.0 g of the HBr salt derivative product. This salt was converted to the free base in an extraction with trichloromethane and aqueous ammonia to give 39.89 g of 1-[1-(2-thienyl)cyclohexyl]-4-hydroxypiperidine (m.p. 123°–125° C.) in 86% yield. TLC analysis of the product showed traces of starting material. A reaction vessel, cooled in an ice bath, was charged with 100 ml of ethanol-free, dry trichloromethane, 12.12 g (122 mmol) of triethylamine and 10.6 g (40 mmol) of 1-[1-(2-thienyl)cyclohexyl]-4-hydroxypiperidine. This mixture was stirred and maintained at a temperature of 10°–20° C. while 5.016 g (44 mmol) of methylsulfonylchloride in 20 ml trichloromethane was added to the reaction vessel. TLC analysis of the reaction mixture showed no unreacted piperidine derivative starting material. The mixture was treated with 250 ml water and 30 ml concentrated ammonium hydroxide. A trichloromethane layer separated which was washed with 250 ml water and 30 ml ammonium hydroxide. Evaporation of the trichloromethane from 50 ml isopropanol yielded 12.89 g of a mesylate derivative. A reaction vessel was charged with 3.43 g of this mesylate derivative, 100 ml tetrahydrofuran and 7.0 eq. of tert-butoxy potassium salt. This mixture was refluxed for 1.5 hour, then successively treated with water, conc. ammonium hydroxide and ethyl ether, and then purified by column chromatography to yield the product compound 1-[1-(2-thienyl)-cyclohexyl]-1,2,5,6-tetrahydropyridine.

EXAMPLE I—PROCEDURE B

A reaction vessel was charged with 41.56 g 1,2,5,6-tetrahydropyridine and 100 ml water. Then 41.74 ml conc. HCl was added to the reaction vessel, followed by addition of 49.07 g of cyclohexanone and 25.62 g sodium cyanide. This reaction mixture was stirred for two days. A two-phase mixture formed to which was added 150 ml ethyl ether. The water layer was discarded. The organic layer was dried over magnesium sulfate and concentrated to give 92.7 g of an oil product (97% yield) identified as 1-(1-cyanocyclohexyl)-1,2,5,6-tetrahydropyridine. A reaction vessel was charged with 26.7 g (1.1 mol) magnesium metal turnings and 150 ml dry ethyl ether. Over a period of 40 minutes, there was added a solution of 40.75 g (250 mmol) 2-bromothiophene in 150 ml ethyl ether. Then, 46.55 g (245 mmol) of 1-(1-cyanocyclohexyl)-1,2,5,6-tetrahydropyridine was added dropwise to the reaction mixture over a period of 2 hours. The mixture was then stirred for 2 days. The reaction mixture was decanted from the magnesium metal into 150 ml water and then 200 ml 1.0N HCl was added to the reaction mixture. To this acidic solution was added 100 ml ethyl ether and 300 ml 1.0N NaOH. The ether layer was dried with sodium sulfate and concentrated. An oily crude product was taken up in 100 ml isopropanol. To this mixture there was added isopropanol saturated with HCl gas in a dropwise manner until the mixture just turned acidic. The crystallized material was recrystallized from isopropanol to give 22.6 g (37.3% yield) of the HCl salt of 1-[1-(2-thienyl)-cyclohexyl]-1,2,5,6-tetrahydropyridine.

Table I is a list of 21 specific compounds of most interest within Formula III. The preparation of Compound No. 1 of Table 1 is described in detail in the alternative Procedures A and B of Example I, above. Compounds No. 2 through 21 may likewise be prepared in accordance with the above-described general synthesis procedures taken with the specific descriptions of Example I, Procedures A and B.

| COMPOUND NO. | FORMAL NAME | STRUCTURE |
|---|---|---|
| 1 | 1-[1-(2-Thienyl)cyclohexyl]-1,2,5,6-tetrahydropyridine | 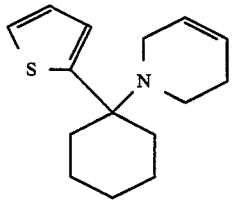 |
| 2 | 1-[1-(2-Thienyl)cyclohexyl]-3-pyrroline | 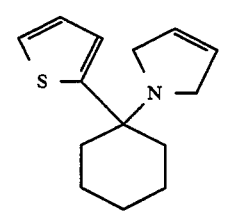 |
| 3 | 1-[1-(2-Thienyl)cyclohexyl]-6-methyl-1,2,5,6-tetrahydropyridine | 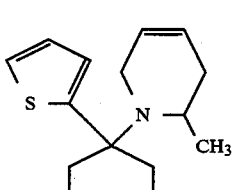 |
| 4 | 1-[1-(2-Thienyl)cyclohexyl]-3-methyl-1,2,5,6-tetrahydropyridine | 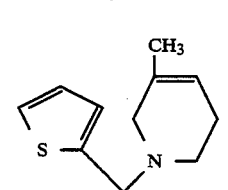 |
| 5 | 1-[1-(3-Methyl-2-thienyl)cyclohexyl]-1,2,5,6-tetrahydropyridine | 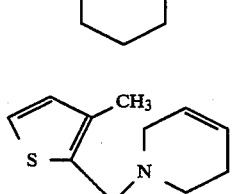 |
| 6 | 1-[1-(4-Methyl-2-thienyl)cyclohexyl]-1,2,5,6-tetrahydropyridine | 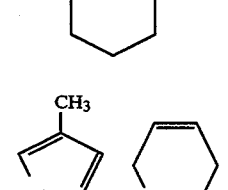 |

-continued

| COMPOUND NO. | FORMAL NAME | STRUCTURE |
|---|---|---|
| 7 | 1-[1-(5-Methyl-2-thienyl)cyclohexyl]-1,2,5,6-tetrahydropyridine | 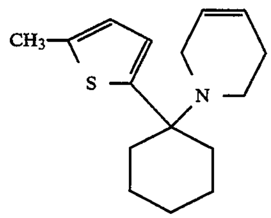 |
| 8 | 1-[1-(3-Thienyl)cyclohexyl]-1,2,5,6-tetrahydropyridine | 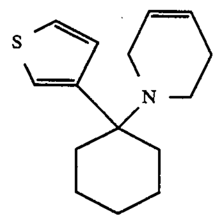 |
| 9 | 1-[1-(2-Thienyl)-4-methylcyclohexyl]-1,2,5,6-tetrahydropyridine | 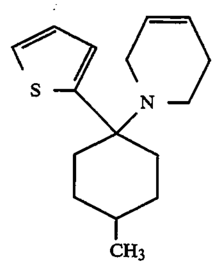 |
| 10 | 1-[1-(2-Thienyl)-4-hydroxycyclohexyl]-1,2,5,6-tetrahydropyridine | 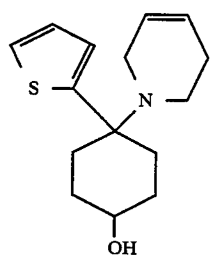 |
| 11 | 1-[1-12-Thienyl)cyclohexyl]-1,2,3,4-tetrahydropyridine | 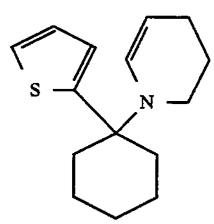 |
| 12 | 1-[1-(3-Thienyl)-4-methylcyclohexyl]-1,2,5,6-tetrahydropyridine | 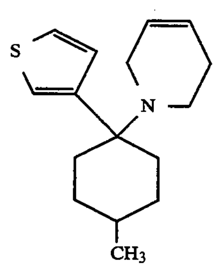 |

-continued

| COMPOUND NO. | FORMAL NAME | STRUCTURE |
|---|---|---|
| 13 | 1-[1-(2-Thienyl)-4-methylcyclohexyl]-3-methyl-1,2,5,6-tetrahydropyridine | 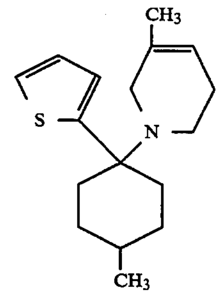 |
| 14 | 1-[1-(5-Methyl-2-thienyl)-4-hydroxycyclohexyl]-1,2,5,6-tetrahydropyridine | 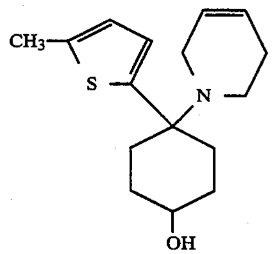 |
| 15 | 1-[1-(3-Thienyl)cyclohexyl]-6-methyl-1,2,5,6-tetrahydropyridine | 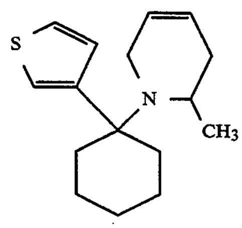 |
| 16 | 1-[1-(2-Thienyl)cyclohexyl]-3,4-dimethyl-1,2,5,6-tetrahydropyridine | 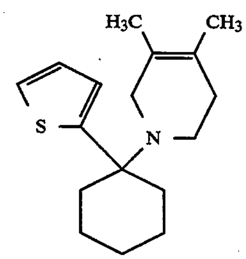 |
| 17 | 1-[1-(2-Thienyl)cyclopentyl]-1,2,5,6-tetrahydropyridine | 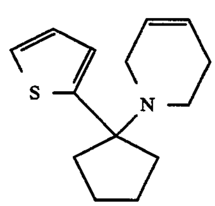 |
| 18 | 1-[1-(5-Methyl-2-thienyl)cyclohexyl]-3-methyl-1,2,5,6-tetrahydropyridine | 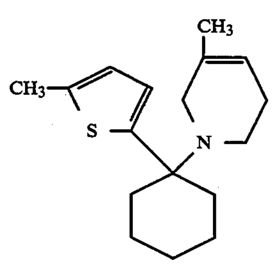 |

-continued

| COMPOUND NO. | FORMAL NAME | STRUCTURE |
|---|---|---|
| 19 | 1-[1-(2-Thienyl)-3-hydroxycyclohexyl]-1,2,5,6-tetrahydropyridine | (structure) |
| 20 | 1-[1-(2-Thienyl)-2-hydroxycyclohexyl]-1,2,5,6-tetrahydropyridine | (structure) |
| 21 | 1-[1-(2-Thienyl)cyclohexyl]-4-methyl-1,2,5,6-tetrahydropyridine | (structure) |

BIOLOGICAL EVALUATION

Prevention of the neurodegenerative consequences associated with conditions of hypoxia or ischemia may be accomplished with administration of a compound of Formula I. In particular, the compound 1-[1-(2-thienyl)-cyclohexyl-1,2,5,6-tetrahydropyridine (Compound No. 1) was evaluated in biological assays to measure the inhibition of hypoxia- or ischemia-induced neuronal toxicity. Compound No. 1, as well as some earlier-known PCP-agonist compounds, were evaluated by various in vivo and in vitro assays to determine compound activity as an NMDA antagonist or PCP agonist. These biological assays, described below, included a radioreceptor assay, a chronic hypoxic insult assay, an acute azide toxicity assay, a glutamate neurotoxicity assay, an NMDA/KA/QUIS antagonist assay, and a behavioral assay.

Radioreceptor Assay

Compound No. 1 was compared against PCP and TCP in an assay to determine the relative potency of the compounds interacting with PCP receptors. To determine the effect of the compounds in a PCP receptor assay, crude membrane preparations were prepared by homogenizing whole rat brains in 30 ml of ice-cold 5 mM Tris-HCl, pH 7.4 (Tris buffer), with a Brinkman Polytron (setting 6, 15 sec). The homogenate was centrifuged twice at $20,000 \times g$ for 15 min at 4° C. with an intervening resuspension of the pellet in cold Tris buffer. The final pellet was resuspended in Tris buffer to obtain a final concentration of 0.1 g of tissue per ml. Incubation tubes were prepared in triplicate and contained 0.1 ml of tissue suspension, 1 nM of $^3$H-TCP and varying concentrations of displacing ligand (0.1–30,000 nM) in a final volume of 0.5 ml. After a 1 hour incubation, the contents of the test tubes were filtered through Schleier & Schuell #32 filters, which had been pre-soaked for at least 2 hours in 0.05% polyethylenimine. The test tubes were rinsed twice and the filters once with 4 ml of tris buffer. Radioactivity on the filters was determined by liquid scintillation spectrometry. Specific binding was defined as the total amount of tritiated compound bound minus the amount bound in the presence of 10 µM of TCP compound. $K_i$ values were determined using the method of Cheng & Prusoff [*Biochem. Pharmacol.*, 22, 3099–3108 (1973)].

| Test Compound | $K_i$ apparent (nM) (units + SEM) |
|---|---|
| PCP | 96 + 15 |
| TCP | 20 + 6 |
| Compound No. 1 | 12 + 2 |

Chronic Hypoxic Insult Assay

Compound No. 1 was tested for its ability to protect hippocampal neurons from hypoxia-induced cell death. Cultures of hippocampal neurons were prepared from embryonic day 17 Sprague-Dawley rats. The hippocampi were dissociated into a single cell suspension by incubation with 0.25% trypsin, 40 mg/ml DNase followed by gentle trituration through a Pasteur pipet. The cells were plated in a polylysine-coated 96-well plate and maintained in a chemically defined medium until use. The cells were grown for 2 to 3 weeks in 5% $CO_2$-in-air humidified environment at 36° C. to establish a thick network of neuronal processes with numerous spontaneously active synapses. Exposure to hypoxic- /anoxic environment was accomplished by placing the cultures in an anaerobic chamber, and flushing it with a mixture of 95% $N_2$+5% $CO_2$ gas to rapidly drop the $O_2$ tension to near zero. The $O_2$ tension was maintained at near zero using a disposable $H_2$+$CO_2$ generator envelope with palladium catalyst. Compound No. 1 was added to the culture medium prior to incubation in the anaerobic chamber and maintained there for 6 hours. Following 2 hours of exposure to normal $O_2$ tension, the cultures were processed for morphological and quantitive biochemical neuronal cell viability assays.

The neuronal survival assay utilized the compound MTT [(3-(4,5-dimethylthiazol-2-yl)-2,5-diphenyl tetrazolium bromide)], a pale yellow substrate that is cleaved by the mitochondrial enzyme succinate-dehydrogenase to yield a dark blue formazan product. This process requires active mitochondria, present only in live cells. Cultures of hippocampal neurons grown in 96-well plates were incubated with 1 mg/ml MTT at 36° C. in a 10% $CO_2$-in-air incubator for 30–60 min. At the end of the incubation, a dark blue precipitate outlined only viable cells. The precipitate was then solubilized using 0.08N HCl/isopropanol mixture and the absorbance measured with an ELISA plate reader (Dynatech MR600) using a test wavelength of 570 nm and a reference wavelength of 630 nm. The resulting optical density is directly proportional to the number of viable cells.

Maximum protection of neurons from hypoxic insult was obtained with 50 $\mu$M of Compound No. 1:

| Sample | Optical Density (units + SDM) |
| --- | --- |
| Untreated Control | 0.163 + .017 |
| Hypoxia | 0.062 + .033 |
| Hypoxia + 50 $\mu$M Compound No. 1 | 0.173 + .033 |

Acute Azide Toxicity Assay

Compound No. 1 was tested for its ability to protect hippocampal neurons from sodium azide poisoning which selectively kills mature neurons while sparing glial cells. Neuronal cells were prepared and the cell viability assays were performed as described in the chronic hypoxia insult assay, above.

Cultures were exposed to 10 $\mu$M sodium azide for 1 hour either in the presence or absence of Compound No. 1 and immediately thereafter processed for qualitative (morphological) and quantitative viability assay. Under this acute and severe toxicity conditions, 1 $\mu$M of Compound No. 1 afforded the neurons significant protection from all death.

| Sample | Optical Density (units + SDM |
| --- | --- |
| Control | 0.146 + .013 |
| Sodium azide | 0.084 + .013 |
| Sodium azide + 1 $\mu$M Compound No. 1 | 0.138 + .013 |

Glutamate Neurotoxicity Assay

Compound No. 1 was tested for its ability to protect neurons from glutamate-induced neurotoxicity, which selectively kills mature neurons while sparing glial cells. Neuronal cells were prepared and cell viability assays were performed as described in the chronic hypoxia insult assay, above.

Hippocampal cultures were exposed to 500 $\mu$M glutamate for 1 hour either in the presence or absence of Compound No. 1 and immediately thereafter processed for qualitative (morphological) and quantitative viability assay. Nearly complete protection from glutamate toxicity was obtained with 50 $\mu$M of Compound No. 1 and significant protection was obtained with 5 $\mu$M.

| Sample | Optical Density (units + SDM) |
| --- | --- |
| Control | 0.163 + .017 |
| 500 $\mu$M glutamate | 0.092 + .017 |
| 500 $\mu$M glutamate + 50 $\mu$M Compound No. 1 | 0.157 + .017 |
| 500 $\mu$M glutamate + 5 $\mu$M Compound No. 1 | 0.147 + .017 |

NMDA/KA Antagonist Assay

A 15-day old chick embryo retina, incubated for 30 min. in a balanced salt solution (BSS) containing 1 mM Glu, developed a full lesion characteristic of an immature mouse retina following s.c. administration of Glu. Other excitotoxin agonists also produce acute lesions within 30 min., each agent being effective at a concentration proportional to its known excitatory and toxic potencies. The pattern of cellular degeneration is restricted in each case to the ganglion cell, inner plexiform and inner nuclear layers, but within these areas certain agonists induce different patterns of degeneration, the differences being most pronounced between NMA and KA. Four agonists were employed in the present test, each at a concentration established previously to be the lowest concentration required to consistently cause a fully-developed retinal lesion: KA (25 $\mu$M), Quis (50 $\mu$M), NMA (200 $\mu$M) and Glu (1000 $\mu$M). Compound No. 1 and other PCP-like compounds were tested at various concentrations for their ability to prevent KA, Quis, NMA or Glu neurotoxicity. Although partial blocking was observed for each antagonist at concentrations below the threshold for complete protection, the criterion used for comparing agents for antagonist potency was the concentration required to completely prevent KA, Quis, NMA or Glu from exerting any toxic activity in any specimen (n>6) studied at that concentration. Internal controls in each experiment consisted of at least six specimens being incubated with agonist alone. A typical toxic reaction had to be present in all controls and absent from all experimental specimens in order to qualify as a blocking effect. The method of tissue preparation was as follows: 15-day old chick embryos were decapitated and their eyes removed and cut into quadrants after excising the cornea and removing the lens, vitreous and iris. The retinal quadrants were then gently separated from the pigment epithelium and incubated for 30 min. at 37° C. in BSS to which an agonist or agonist plus antagonist was added. The BSS contained 140 mM $Na^+$, 5.0 mM $K^+$, 0.5 mM $Ca^{++}$, 4.5 mM $Mg^{++}$, 150 mM $Cl^-$, 5.6 mM glucose and bicarbonate/phosphate buffer (pH 7.3). After incubation for 30 min., the retinal quadrants were fixed by immersion in phosphate-buffered solution containing 1.5% glutaraldehyde and 1% paraformaldehyde, then additionally fixed in 1% osmium tetroxide, dehydrated in graded ethanols, cleared in toluene and embedded in araldite. Sections were cut 1 micron thick on a Sorval ultratome and stained with methylene blue/Azure 11 for histopathological evaluation by light microscopy.

TABLE 1

POTENCIES OF ANTAGONISTS IN BLOCKING NMA, KA, QUIS OR GLU NEUROTOXICITY

Compounds were rated according to the minimal concentration ($\mu$M) required to provide total protection against NMA (200 $\mu$M), KA (25 $\mu$M), Quis (50 $\mu$M) or Glu (1000 $\mu$M). Antagonists were tested over a range of concentrations from 1000 $\mu$M downward until a minimal effective concentration was established.

| Potential antagonist | vs NMA | vs KA | vs Quis* |
|---|---|---|---|
| PCP | 1 $\mu$M | No Activity | No Activity |
| Metaphit | 50 $\mu$M | No Activity | No Activity |
| Compound No. 1 | 0.25 $\mu$M | Partial @ 5 $\mu$M Zero @ 250 $\mu$M | |

*@ up to 500 $\mu$M

Behavioral Assay

Compound No. 1 was tested in comparison with PCP and TCP by an in vivo assay which determined stereotypic behavior in rats treated with the compounds. Male Sprague-Dawley rats weighing 200 to 250 g were used in the behavioral experiments. Each rat was used only once. Rats were anesthetized lightly with ether before a 20-gauge needle was used to make a hole in the rat's skull for i.c.v. injection of drugs at a later date. The rats were allowed to recover for at least 1 day before being used in the behavioral assays. On the day of the experiment, rats were placed individually into plastic rat cages and allowed at least 1 hr to acclimate before testing. Drugs were administered to rats in a random, single-blind fashion. Behavioral ratings were taken at 5-min intervals up to 1 hr after drug administration i.c.v. using the PCP rating scale as described by Sturgeon et al [Sturgeon, R. D., Fessler, R. G. and Meltzer, H. Y., "Behavioral Rating Scales for Accessing Phencyclidine-Induced Locomotor Activity, Stereotyped Behavior And Ataxia In Rats", *European J. Pharmacol.* 59 169, ( 1970 ) ]. Briefly, the rating scale for stereotyped behavior is: 0, inactive or nonrepetitive activity; 1, sniffing, grooming or rearing; 2, nondirectional movements, and occasional reciprocal forepaw treading; 3, circling or head-weaving behavior or backpeddling; 4, rapid and continuous circling or head-weaving behavior, assuming a praying posture or gagging; and 5, dyskinetic extension and flexion of limbs, head and neck or head-weaving greater than in "4."

Dose-response curves for each treatment were determined at the time of maximal behavioral effect. Peak effects were found 5 min after i.c.v. administration of PCP (25–20000 nmol/rat). Peak effects of PCP (2.0–32 mg/kg) after i.p. administration were observed at 15 min. A rating of 5 in the PCP-rating scale was considered as complete stereotyped behavior, that is, a 100% response. At least 21 rats (at least seven rats/dose) were used to determine each dose-response curve and $ED_{50}$ values. $ED_{50}$ values and dose-response curves were evaluated using a computerized Finney assay [*Statistical Methods In Biological Assays,* 2nd Edn., Hatner Pub. Co., New York (1964)].

The ability of the tested compounds to induce stereotyped behavior was assessed at 2.5, 5 and 10 minutes and thereafter every 5 min up to 1 hr after i.c.v., i.p., or s.c. administration. Results are as follows:

| | Stereotyped Behavior $ED_{50}$ (nmol/rat) |
|---|---|
| PCP | 150 (120–180)[a] |
| TCP | 56 (49–76)[a] |
| Compound No. 1 | 43 (34–57)[a] |

[a]Values in parentheses are 95% confidence intervals.

Administration of compounds within Formula I to humans can be by any technique capable of introducing the compounds into the bloodstream of a human patient, including oral administration, and by intravenous, intramuscular and subcutaneous injections.

Compounds indicated for prophylactic therapy will preferably be administered in a daily dose generally in a range from about 0.1 mg to about 10 mg per kilogram of body weight per day. A more preferred dosage will be a range from about 0.2 mg to about 5 mg per kilogram of body weight. Most preferred is a dosage in a range from about 0.3 to about 2.5 mg per kilogram of body weight per day. A suitable dose can be administered in multiple sub-doses per day. These sub-doses may be administered in unit dosage forms. Typically, a dose or sub-dose may contain from about 1 mg to about 100 mg of active compound per unit dosage form. A more preferred dosage will contain from about 2 mg to about 50 mg of active compound per unit dosage form. Most preferred is a dosage form containing from about 3 mg to about 25 mg of active compound per unit dose.

The active compound is usually administered in a pharmaceutically-acceptable formulation, although in some acute-care situations a compound of Formula I may be administered alone. Such formulations may comprise the active compound together with one or more pharmaceutically-acceptable carriers or diluents. Other therapeutic agents may also be present in the formulation. A pharmaceutically-acceptable carrier or diluent provides an appropriate vehicle for delivery of the active compound without introducing undesirable side effects. Delivery of the active compound in such formulations may be by various routes including oral, nasal, topical, buccal and sublingual, or by parenteral administration such as subcutaneous, intramuscular, intravenous and intradermal routes.

Formulations for oral administration may be in the form of capsules containing the active compound dispersed in a binder such as gelatin or hydroxypropylmethyl cellulose, together with one or more of a lubricant, preservative, surface-active or dispersing agent. Such capsules or tablets may contain a controlled-release formulation as may be provided in a disposition of active compound in hydroxypropylmethyl cellulose.

Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. Compound of the formula

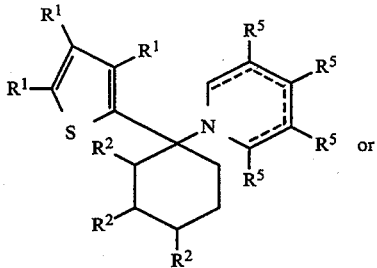

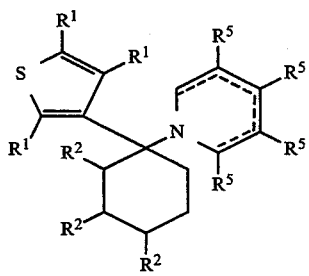

wherein each $R^1$ is independently hydrido, alkyl of one to ten carbon atoms, cycloalkyl of three to ten carbon atoms, alkenyl of two to ten carbon atoms, hydroxyl, alkoxy or halo, wherein at least two of said $R^1$ groups are hydrido;

each $R^2$ is independently hydrido, alkyl of one to ten carbon atoms, cycloalkyl of three to ten carbon atoms, alkenyl of two to ten carbon atoms, hydroxyl, oxo, alkoxy or halo, wherein at least two of said $R^2$ groups are hydrido;

each $R^5$ is independently hydrido, alkyl of one to ten carbon atoms, cycloalkyl of three to ten carbon atoms, alkenyl of two to ten carbon atoms, hydroxyl or alkoxy, wherein at least two of said $R^5$ groups are hydrido; and wherein the broken line within the N-containing ring represents a double bond between any two adjacent carbon atoms involving the 2-, 3-, 4-, 5-, and 6-positions of said N-containing ring.

2. Compound of claim 1 of the formula

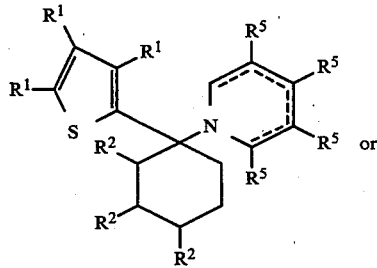

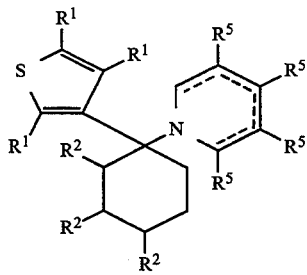

wherein each $R^1$ is independently hydrido, alkyl of one to five carbon atoms, cycloalkyl of three to five carbon atoms, alkenyl of two to five carbon atoms, hydroxyl or alkoxy, wherein at least two of said $R^1$ groups are hydrido;

each $R^2$ is independently hydrido, alkyl of one to five carbon atoms, cycloalkyl of three to five carbon atoms, alkenyl of two to five carbon atoms, hydroxyl, oxo or alkoxy, wherein at least two of said $R^2$ groups are hydrido;

each $R^5$ is independently hydrido, alkyl of one to five carbon atoms, cycloalkyl of one to five carbon atoms, alkenyl of two to five carbon atoms, hydroxyl or alkoxy, wherein at least two of said $R^5$ groups are hydrido; and wherein the broken line within the N-containing ring represents a double bond between any two adjacent carbon atoms involving the 3-, 4-, and 5-positions of said N-containing ring.

3. Compound of claim 2 wherein each $R^1$ is independently hydrido, methyl, cyclopropyl or ethyl, wherein at least two of said $R^1$ groups are hydrido; wherein each $R^2$ is independently hydrido, hydroxyl, methyl, ethyl or cyclopropyl, wherein at least two of said $R^2$ groups are hydrido; and wherein each $R^5$ is independently hydrido, methyl, ethyl or cyclopropyl, wherein at least two of said $R^5$ groups are hydrido.

4. Compound of claim 3 which is 1-[1-(2-thienyl)cyclohexyl]-1,2,5,6-tetrahydropyridine.

5. A pharmaceutical composition comprising a therapeutically-effective amount of a compound to treat or prevent a neurodegenerative disease and a pharmaceutically-acceptable carrier or diluent, said compound having the formula

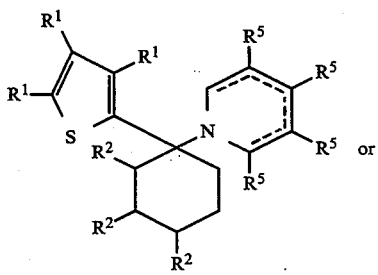

-continued

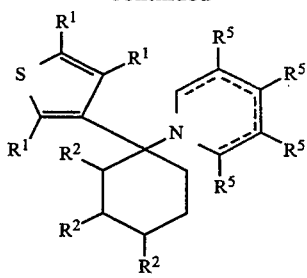

wherein each $R^1$ is independently hydrido, alkyl of one to ten carbon atoms, cycloalkyl of three to ten carbon atoms, alkenyl of two to ten carbon atoms, hydroxyl, alkoxy or halo, wherein at least two of said $R^1$ groups are hydrido;

each $R^2$ is independently hydrido, alkyl of one to ten carbon atoms, cycloalkyl of three to ten carbon atoms, alkenyl of two to ten carbon atoms, hydroxyl, oxo, alkoxy or halo, wherein at least two of said $R^2$ groups are hydrido;

each $R^5$ is independently hydrido, alkyl of one to ten carbon atoms, cycloalkyl of three to ten carbon atoms, alkenyl of two to ten carbon atoms, hydroxyl or alkoxy, wherein at least two of said $R^5$ groups are hydrido; and wherein the broken line within the N-containing ring represents a double bond between any two adjacent carbon atoms involving the 2-, 3-, 4-, 5-, and 6-positions of said N-containing ring.

6. Composition of claim 5 wherein said compound is of the formula

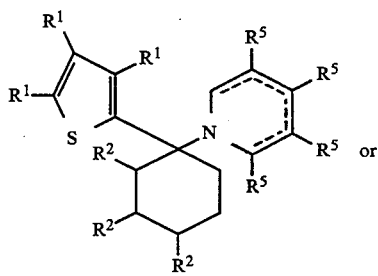

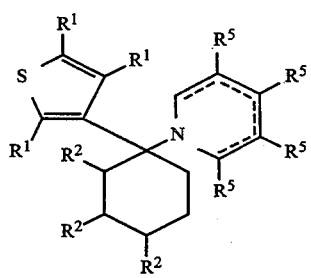

wherein each $R^1$ is independently hydrido, alkyl of one to five carbon atoms, cycloalkyl of three to five carbon atoms, alkenyl of two to five carbon atoms, hydroxyl or alkoxy, wherein at least two of said $R^1$ groups are hydrido;

each $R^2$ is independently hydrido, alkyl of one to five carbon atoms, cycloalkyl of three to five carbon atoms, alkenyl of two to five carbon atoms, hydroxyl, oxo or alkoxy, wherein at least two of said $R^2$ groups are hydrido;

each $R^5$ is independently hydrido, alkyl of one to five carbon atoms, cycloalkyl of one to five carbon atoms, alkenyl of two to five carbon atoms, hydroxyl oralkoxy, wherein at least two of said $R^5$ groups are hydrido; and wherein the broken line within the N-containing ring represents a double bond between any two adjacent carbon atoms involving the 3-, 4-, and 5-positions of said N-containing ring.

7. Composition of claim 6 wherein each $R^1$ is independently hydrido, methyl, cyclopropyl or ethyl, wherein at least two of said $R^1$ groups are hydrido; wherein each $R^2$ is independently hydrido, hydroxyl, methyl, ethyl or cyclopropyl, wherein at least two of said $R^2$ groups are hydrido; and wherein each $R^5$ is independently hydrido, methyl, ethyl or cyclopropyl, wherein at least two of said $R^5$ groups are hydrido.

8. Composition of claim 5 wherein said compound is 1-[1-(2-thienyl)cyclohexyl]-1,2,5,6-tetrahydropyridine.

9. Composition of claim 5 wherein said compound is selected for treatment or prevention of neuronal degeneration due to ischemic, hypoxic or anoxic conditions.

10. Method to control neuropathological processes and the neurodegenerative consequences thereof in mammals, which method comprises treating a mammal susceptible to neurotoxic injury with an effective amount of a compound of the formula

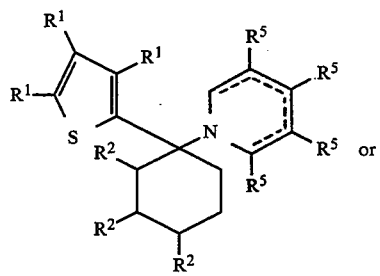

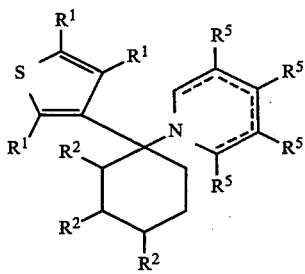

wherein each $R^1$ is independently hydrido, alkyl of one to ten carbon atoms, cycloalkyl of three to ten carbon atoms, alkenyl of two to ten carbon atoms, hydroxyl, alkoxy or halo, wherein at least two of said $R^1$ groups are hydrido;

each $R^2$ is independently hydrido, alkyl of one to ten carbon atoms, cycloalkyl of three to ten carbon atoms, alkenyl of two to ten carbon atoms, hydroxyl, oxo, alkoxy or halo, wherein at least two of said $R^2$ groups are hydrido;

each $R^5$ is independently hydrido, alkyl of one to ten carbon atoms, cycloalkyl of three to ten carbon atoms, alkenyl of two to ten carbon atoms, hydroxyl or alkoxy, wherein at least two of said $R^5$ groups are hydrido; and wherein the broken line within the N-containing ring represents a double bond between any two adjacent carbon atoms involving the 2-, 3-, 4-, 5-, and 6-positions of said N-containing ring.

11. Method of claim 10 wherein said compound is of the formula

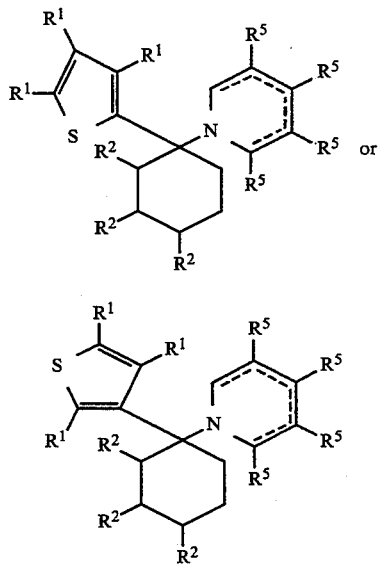

wherein each R¹ is independently hydrido, alkyl of one to five carbon atoms, cycloalkyl of three to five carbon atoms, alkenyl of two to five carbon atoms, hydroxyl or alkoxy, wherein at least two of said R¹ groups are hydrido;

each R² is independently hydrido, alkyl of one to five carbon atoms, cycloalkyl of three to five carbon atoms, alkenyl of two to five carbon atoms, hydroxyl, oxo or alkoxy, wherein at least two of said R² groups are hydrido;

each R⁵ is independently hydrido, alkyl of one to five carbon atoms, cycloalkyl of one to five carbon atoms, alkenyl of two to five carbon atoms, hydroxyl or alkoxy, wherein at least two of said R⁵ groups are hydrido; and wherein the broken line within the N-containing ring represents a double bond between any two adjacent carbon atoms involving the 3-, 4-, and 5-positions of said N-containing ring.

12. Method of claim 11 wherein each R¹ is independently hydrido, methyl, cyclopropyl or ethyl, wherein at least two of said R¹ groups are hydrido; wherein each R² is independently hydrido, hydroxyl, methyl, ethyl or cyclopropyl, wherein at least two of said R² groups are hydrido; and wherein each R⁵ is independently hydrido, methyl, ethyl or cyclopropyl, wherein at least two of said R⁵ groups are hydrido.

13. Method of claim 10 wherein said compound is 1-[1-(2-thienyl)cyclohexyl]-1,2,5,6-tetrahydropyridine.

* * * * *